United States Patent [19]

Mensink et al.

[11] Patent Number: 4,627,022
[45] Date of Patent: Dec. 2, 1986

[54] PACEMAKER UTILIZING MICROPROCESSOR DMA FOR GENERATING OUTPUT PULSE SEQUENCES

[75] Inventors: Kornelis A. Mensink, Brummen; Henk L. Brouwer, Dieren, both of Netherlands

[73] Assignee: Vitafin N.V., Curacao, Netherlands Antilles

[21] Appl. No.: 417,167

[22] Filed: Sep. 13, 1982

[30] Foreign Application Priority Data

Oct. 26, 1981 [EP] European Pat. Off. ........ 81108939.0

[51] Int. Cl.⁴ .......................... A61N 1/36; G06F 1/04
[52] U.S. Cl. .................................... 364/900
[58] Field of Search ................... 128/419 P, 419 PG; 364/200, 900, 200 MS File, 900 MS File

[56] References Cited

U.S. PATENT DOCUMENTS

| | | | |
|---|---|---|---|
| 3,740,728 | 6/1973 | Pullen | 364/200 |
| 4,137,565 | 1/1979 | Mager et al. | 364/200 |
| 4,203,543 | 5/1980 | Staiger | 364/900 |
| 4,313,441 | 2/1982 | Buffet | 128/419 PG |
| 4,390,022 | 6/1983 | Cazfee et al. | 128/419 PG |

FOREIGN PATENT DOCUMENTS 2494119  5/1982  France .
2026870  2/1980  United Kingdom .

OTHER PUBLICATIONS

Motorola, *MC68000 Family Product Literature*, Mar. 1981.

*Primary Examiner*—Gareth D. Shaw
*Assistant Examiner*—Daniel K. Dorsey
*Attorney, Agent, or Firm*—Woodcock Washburn Kurtz Mackiewicz & Norris

[57] ABSTRACT

Apparatus for producing programmable timing signals, having a microprocessor element with means for carrying out DMA operations when said microprocessor element is in a DMA mode, memory interconnected with said microprocessor element and containing a stored program and a plurality of data words stored at predetermined addresses for selection by said microprocessor when in said DMA mode, comprising controller means for transforming received data words into timing signals, connecting means for interconnecting said microprocessor element, said controller and said memory, said controller having means for setting said microprocessor in said DMA mode upon receipt of a predetermined signal generated by said program, means for receiving data words directly from said memory under control of said microprocessor when said microprocessor is in said DMA mode, and means for generating a two state timing signal corresponding to the data content of one or more such received data words. Hereby the operability of the pacer is improved whereas simultaneously low power requirements are maintained.

12 Claims, 4 Drawing Figures

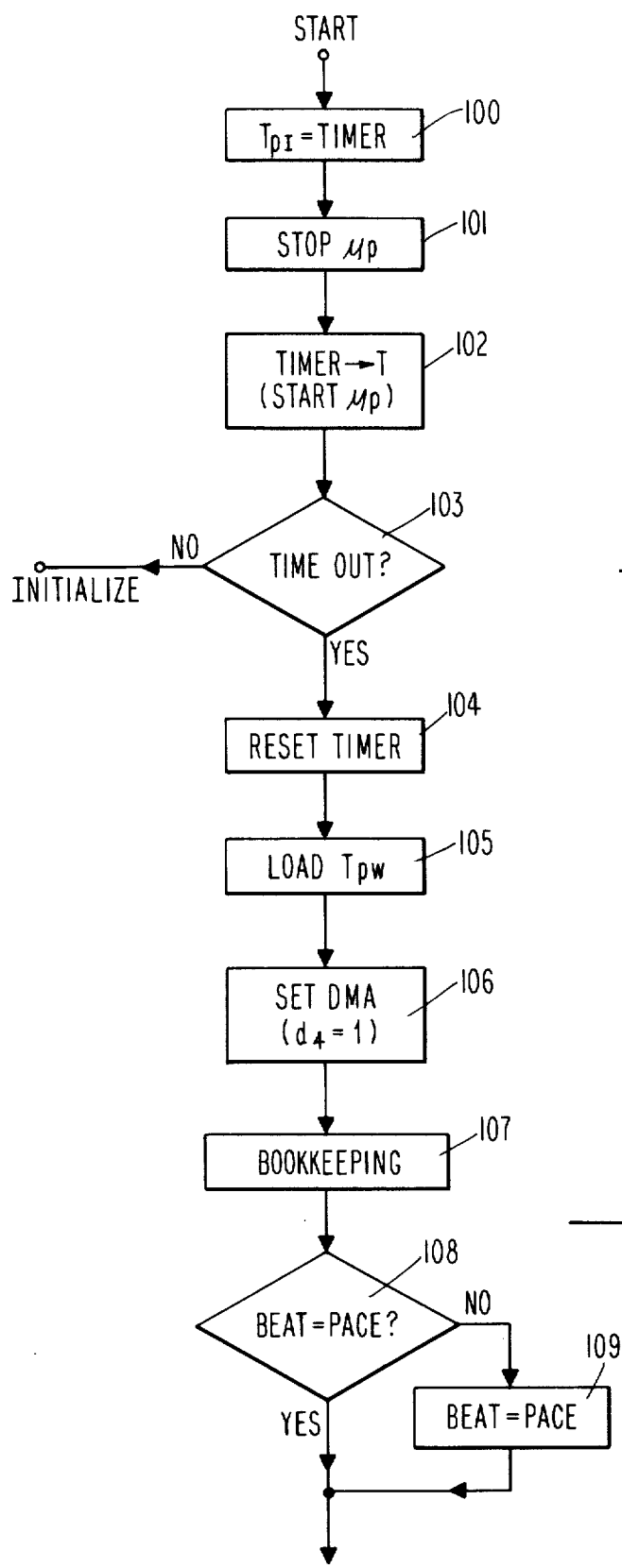
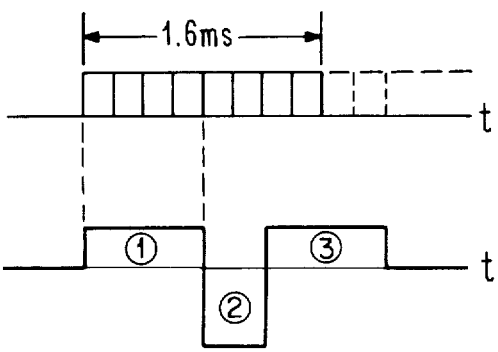
Fig. 4
Fig. 3

PACEMAKER UTILIZING MICROPROCESSOR DMA FOR GENERATING OUTPUT PULSE SEQUENCES

BACKGROUND OF THE INVENTION

This invention relates to apparatus for programmed generation of timing signals and, in particular, programmable microprocessor-controlled pacemaker apparatus.

The evolution of pacemaker design has led to the incorporation of the microprocessor into the pacemaker apparatus, as a means for providing flexible programming of the pacemaker operation. The incorporation of a microprocessor into a cardiac pacer has been made possible by the development of a relatively low power single chip CPU. For example, the CDP 1802 employs CMOS technology, operates at relatively low power with a single power supply, and has a broad operating temperature range. For a pacemaker application, such a microprocessor is well suited for carrying out the desired sub-routines, interrupts and data access in general, and provides good capability for software control of the pacer operation. Even for a relatively simple modern day pacemaker, which operates only in one or a limited number of pacing modes, it is highly desirable to be able to program multiple parameters of the pacer operation, thus strongly indicating software control such as is provided by a microprocessor.

As is well known by those familiar with operation of microprocessors, the basic machine cycle and thus the speed of carrying out instructions is controlled by the rate of the clock pulses which establish the timing operation of the microprocessor. Further, for a CMOS microprocessor, power consumption is a direct function of the clock rate, the power drain being directly proportional to the clock rate due to the nature of CMOS switching. Thus, a tradeoff is presented as between the desire for a low power drain and the desire for a short instruction execution time, the latter requiring a high clock rate. Thus, to the extent it is compatible with carrying out the operating and house keeping functions required by the pacemaker, it is desired to minimize the clock rate so as to minimize power drain. Since normal pacing and natural heartbeat rates are in the order of 70 beats per minute, and the maximum allowable rate is usually set in the area of 120-150 per minute, more than sufficient time to carry out all microprocessor operations is available with a clock rate of 40 KHz, corresponding to a 25 microsecond clock interval. However, for the CDP 1802 each instruction requires 16 clock pulses, consisting of two 8-clock pulse machine cycles. Thus, a single instruction using this microprocessor takes 16 clock intervals, which equates to 400 microseconds for a 40 KHz clock. Thus, the minimum time unit for carrying out any software control operation is 400 microseconds, meaning that operations cannot be carried out with any greater time resolution. Indeed, most operations which incorporate communicating an output from the microprocessor require at least three such instructions, making the minimum resolution 1200 microseconds, or 1.2 ms. Thus, it is seen that for software controlled operations, operation of the clock generator at a relatively low frequency has the advantage of minimizing current drain, but this advantage is gained only with the relative loss of speed in carrying out desired operations.

More specifically, in the pacer application there is a need for generating signals which are time controlled, such as the periodic output stimulus pulse, blanking intervals, etc. Generation of these signals requires electronic circuits, suitably on a separate chip from the microprocessor, which are controlled by software generated outputs delivered at designated microprocessor output pins and connected to the control chip. In order to utilize the versatility of the microprocessor, it is desired that these signals be software controlled, i.e., generated by specific sub-routines as stored in memory associated with the microprocessor. However, if the minimum time unit within which the microprocessor program can operate is greater than time intervals for the output signals, there is a conflict between the application needs and the software capability. Also, if a sequence of output pulses is desired, the normal software is unable to control generation of such sequences without time gaps during which necessary microprocessor instructions are carried out. There is thus a need for a means of interfacing the microprocessor capability with the specific additional electronic circuitry of the pacer, in order to achieve the desired time responses necessary for the pacer application.

BRIEF SUMMARY OF THE INVENTION

It is an object of this invention to provide a microprocessor controlled multi-programmable pacer characterized by software control of the primary pacer operations.

It is another object of this invention to provide a pacer having relatively high speed output switching which is carried out under the control of stored software.

It is another object of this invention to provide a microprocessor controlled pacemaker capable of providing high speed output pulses, with relatively low microprocessor power consumption.

It is another object of this invention to provide a microprocessor controlled pacer which produces programmed output sequences, and having means for driving the microprocessor with a relatively low clock rate.

It is another object of this invention to provide a software controlled pacemaker apparatus providing programmability of complex timing sequences with high speed resolution.

It is another object of this invention to provide a low power consumption microprocessor controlled pacer with high time resolution software control of pacer signals.

It is another object of this invention to provide pacer apparatus having software controlled timing signal outputs of predetermined sequences, such outputs being provided at selected ones of multiple control lines.

In accordance with the above invention, there is provided a pacer utilizing a microprocessor CPU and associated memory, the microprocessor having a DMA mode, a separate controller circuit adapted to interface with said microprocessor and memory, the controller having means for placing said microprocessor in a DMA mode whereby programmed sequences of data signals are connected directly to said controller circuitry, and means for converting said sequences of data signals into programmed timing signals. The controller circuitry and the microprocessor are driven by a relatively low rate clock, the clock interval defining the time resolution of the output timing signals thus generated.

BRIEF DESCRIPTION OF THE DRAWINGS

FIG. 3 is a flow diagram of a simple microprocessor fixed rate routine for a pacer, illustrating generation of output signals under DMA control.

FIG. 4 illustrates timing signals and a representative timing signal output made available by use of this invention.

DESCRIPTION OF THE PREFERRED EMBODIMENT

Figure 1:
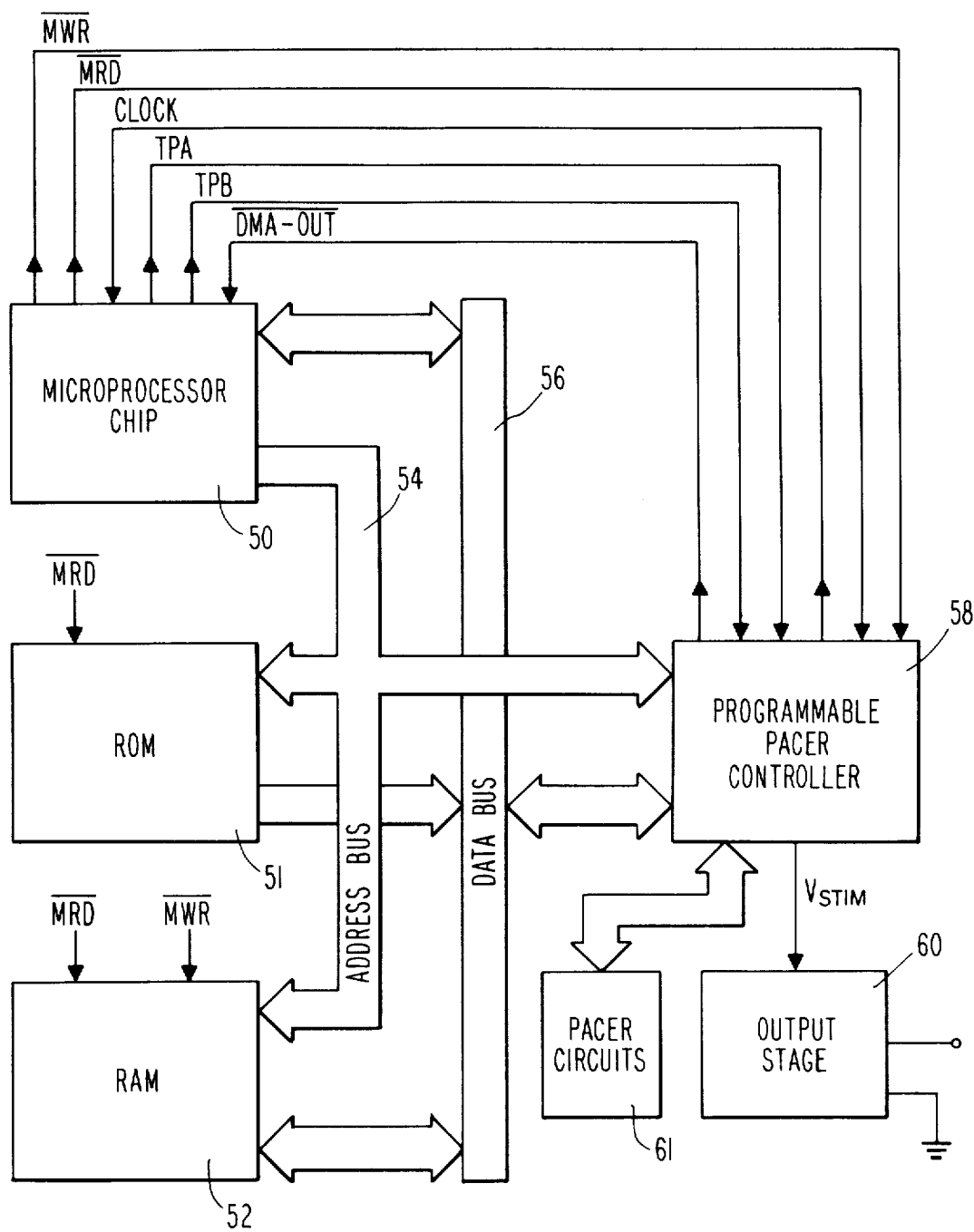
FIG. 1 is a block diagram showing the main portions of the pacer which are pertinent to this invention, including the microprocessor and the programmable pacer controller circuitry, and interconnection between the same.

Referring now to FIG. 1, there is shown a block diagram of the primary components of the apparatus of this invention. Shown in block 50 is a microprocessor chip, and as used hereinafter the term microprocessor or microprocessor element means a commercially available microprocessor, whether of one or more chips. A preferred microprocessor for use in the application of this invention as part of a programmable cardiac pacer is the CDP 1802 microprocessor made by RCA. The CDP 1802, hereinafter the 1802, is fabricated on a single chip utilizing a silicon gate CMOS structure. Because of its CMOS structure it offers the design advantages of wide operating temperature range, relatively high speed, high noise immunity and in particular low power consumption. It is to be understood that particularly for an implantable pacer application, where the lifetime of the battery source is important, the low power CMOS microprocessor is particularly advantageous. Another CMOS microprocessor suitable for use in this invention is the Hitachi 8080A, which is used together with DMA controller chip 8257-5. As used herein, the phrase microprocesor having a DMA mode means equally the one chip type such as the 1802, or the two chip type such as the 8080A and the 8257-5.

Descriptions and specifications of the CDP 1802 are freely available and in the technical literature, and accordingly a full description of the microprocessor is not necessary in the specification. However, some further comments are useful for clarifying the description of this invention. The CDP 1802 has a 40 pin circuit. A standard bidirectional parallel data bus 56 utilizes 8 pins, BUS 0–BUS 7. All parallel data communications between the CPU and external logic, memory or I/O occur via this data bus. There is an 8 bit address bus, represented by the numeral 54. All addresses must be multiplexed; the high order address byte is first outputted, followed by the low order address byte. It is to be noted that compatible memory is used with the CDP 1802 which includes address decode logic. There are 7 status flag pins, including Data Flag and Interrupt Enable Flag, 4 I/O flags and a Q Status Flag which can be set or reset directly by appropriate instructions. There are 4 timing signals, namely CLOCK, $\overline{\text{XTAL}}$, $\overline{\text{TPA}}$ and $\overline{\text{TPB}}$, the latter three being shown in FIG. 1. CLOCK is the principle timing signal, input from a clock found in programmable pacer controller 58 and controlled by logic within that controller. The frequency of the clock may be up to 6.4 MHz, but for this application is 40 KHz. When using the on-chip clock logic of the microprocessor, an external crystal must be connected with a parallel resistor to the $\overline{\text{XTAL}}$ and clock pins. $\overline{\text{TPA}}$ and $\overline{\text{TPB}}$ are timing pulses output by the microprocessor each machine cycle, to control external logic. The remaining pins are control pins, only three of which are illustrated here. $\overline{\text{MWR}}$ and $\overline{\text{MRD}}$ control the memory operation. $\overline{\text{MWR}}$ is output as a low pulse after the second (low order) byte of an address has been placed on the address bus. $\overline{\text{MWR}}$ indicates a memory access operation. $\overline{\text{MRD}}$ indicates the direction of data access; if $\overline{\text{MRD}}$ is low, then the microprocessor is reading data from memory or I/O devices, while if MRD is high, then the microprocessor is writing to memory or I/O devices.

The remaining control line shown connected to a pin of the microprocessor is $\overline{\text{DMA-OUT}}$. The CDP 1802 has a simple direct memory access (DMA) which is utilized by loading the appropriate desired memory address into a general purpose register RO. The register RO is thus set aside to be available for direct memory access when programmed. External logic, in this application provided from controller 58, causes data to be transferred to or from memory, by putting the microprocessor in the DMA mode. Inputting a low pulse at the $\overline{\text{DMA-IN}}$ pin (not shown) permits direct data transfer to memory, and inputting low pulses at the $\overline{\text{DMA-OUT}}$ pin permits direct data transfer from memory to an external circuit. In the present application, DMA is utilized to transfer data from predetermined memory locations in ROM 51 directly to the controller circuit 58, as discussed in more detail below.

In the basic timing operation of the CDP 1802, each instruction is fetched on the first machine cycle (8 clock pulses) and executed during the second cycle, except for two instructions that require two machine cycles for execution. In the DMA mode, when the external logic calls for DMA transfer one or more machine cycles are "stolen" at the end of the execute machine cycle of the then current instruction. During the first such stolen cycle, the data in the address indicated by register RO, which is used as the DMA data pointer, is tranferred directly to the external circuit, and RO is incremented so that the processor is ready for the next DMA request. As long as $\overline{\text{DMA-OUT}}$ stays low, the transfer will continue.

Still referring to FIG. 1, the address bus 54 is shown interconnected with ROM memory 51, RAM memory 52, and the programmable pacer controller circuit 58. The ROM is suitably an RCA model CPD 1833 chip while the RAM is suitably an RCA model CDP 1822 chip. The data bus 56 interconnects the microprocessor chip 50 with ROM 51, RAM 52 and pacer controller 58. Although only one ROM and one RAM block are shown, it is to be understood that there is no limitation on the amount of memory, subject only to design considerations. As further shown in FIG. 1, the output of controller block 58, which is a timing signal represented as $V_{stim}$, is connected to a conventional output stage 60 for developing an output signal to be delivered to a patient's heart. It is to be understood that for a pacer application other conventional circuitry is incorporated, including timing logic for determining the rate and circumstances for delivering output pulses; an input path for receiving natural heart signals and amplifying same; receiving means for receiving external program signals and modifying operating parameters in accordance with such external signals; etc. All these functions are conventional and well described in the patent literature, and are represented by block 61 which is shown communicating with controller 58.

Figure 2:
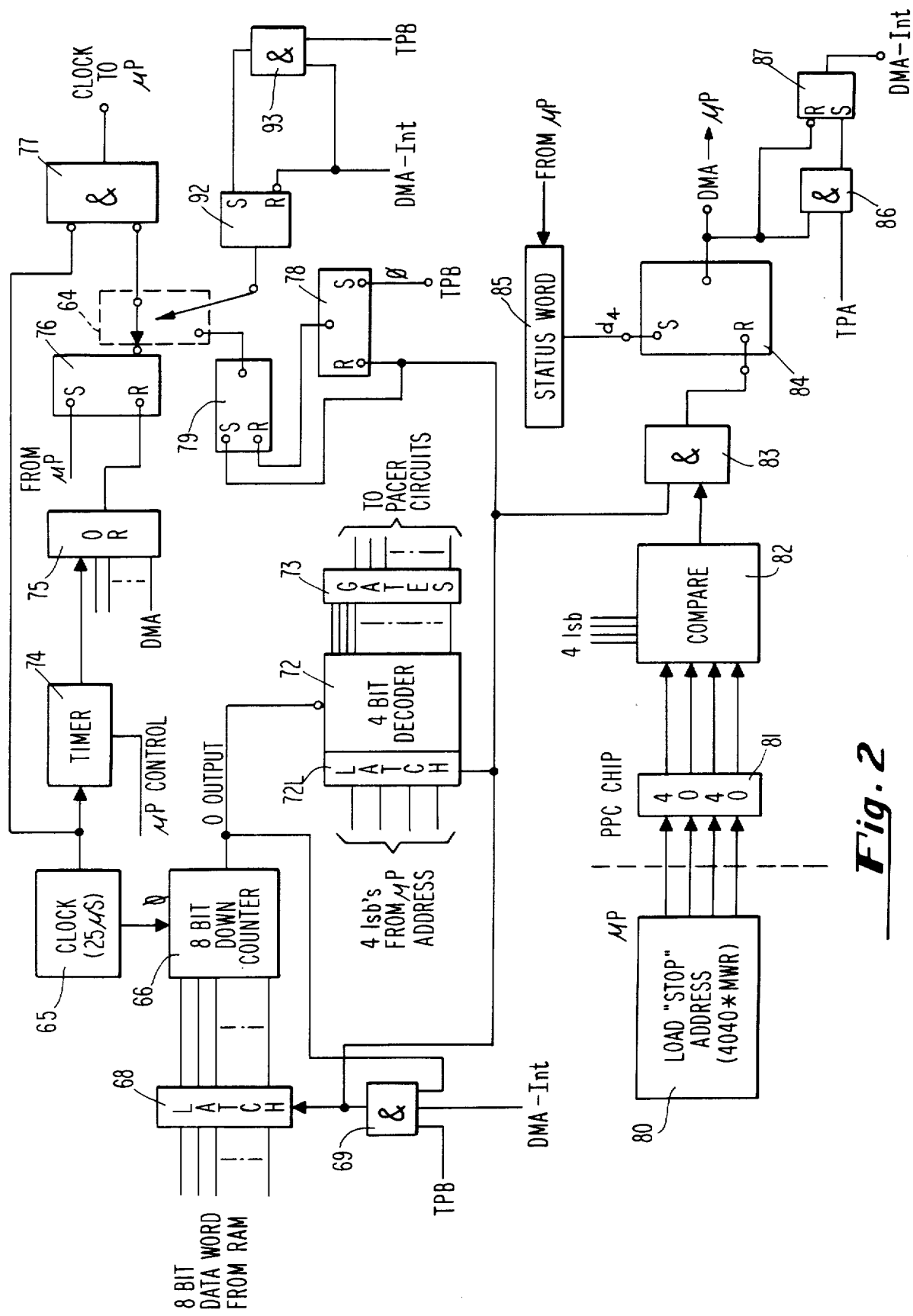
FIG. 2 is a more detailed block diagram indicating circuitry of the pacer controller for generating output pulse signals derived from data words delivered from memory when under microprocessor DMA control, and for controlling the DMA mode of the microprocessor.

Referring now to FIG. 2, there is shown a more detailed diagram representing the portions of pacer controller 58 which are utilized in this invention. When the program reaches a DMA instruction, the microprocessor generates and transfers to controller 58 a status word which is stored in location 4000, shown at block 85 in FIG. 2, which word has bit d4 set high (d4=1). When bit d4 goes high, flip flop 84 is set, thereby generating a DMA high signal at its output. This signal is inverted and connected to the microprocessor $\overline{\text{DMA-OUT}}$ line, to place it into the DMA mode. The DMA signal for 84 is connected through AND gate 86 and flip flop 87, to provide a delayed DMA-Int signal upon the next occurence of a TPA pulse.

Still referring to the bottom path of FIG. 2, the program loads a "stop" address into address location 4040, illustrated in block 81 on the PPC chip. This loading step can be done at any time desired in the program, using a memory write instruction, prior to generating the timing signal while in the DMA mode. The address loaded into memory location 81 is programmed to correspond to the last address in the sequence of addresses to be utilized in the DMA operation. The four least signficant bits from each address generated by the microprocessor while in the DMA mode are inputted into compare circuit 82, and compared with the stored address in memory location 81. When the comparison is made, indicating that the last data word to be transferred under DMA control has indeed been transferred, AND gate 83 is enabled, and an output is produced at the next zero output countdown of counter 66, which indicates the end of the DMA operation. This output from AND gate 83 is connected to the reset terminal of logic flip flop 84, which causes the DMA signal to terminate. Thus, when the program initially calls for the DMA mode the output of flip flop 84 switches to provide a $\overline{\text{DMA-OUT}}$ low signal, which signal maintains DMA operation until flip flop 84 is reset following the end of generation of the programmed timing signal.

When microprocessor 50 is controlled in the DMA-OUT mode, an 8 bit data word is selected from a predetermined start address in ROM, which address has been placed into the RO counter of the microprocessor under program control. Upon occurrence of a TPB timing pulse from the microprocessor, the data word is latched at latch 68 and inputted to an 8 bit down counter 66. Thus, counter 66 is loaded with a particular 8 bit word depending upon what had been stored at the selected memory location. When the DMA mode starts, it takes the microprocessor 8 clock cycles to go to the first address in memory and put its 8 bit data word on the data bus. The delayed DMA-Int signal is connected to one input of AND gate 69, such that it is not enabled until the data word is on the bus. Since counter 66 is initially at zero output, latch 68 receives a latching signal from gate 69 only when the next TPB pulse arrives, at which time the first transferred data word is loaded into counter 66. Counter 66 is clocked down by clock pulses from generator 65, which in this application are delivered at 25 micro second intervals. When the counter counts down to zero, a high ZERO OUTPUT signal is connected to an input of gate 69 and to the enable terminal of four bit decoder 72. As long as the ZERO OUTPUT signal is low, decoder 72 is enabled. The address from register RO of the microprocessor is also communicated to the controller, and the four least significant bits are latched into decoder 72 through latch 72L. Decoder 72 provides a high output on one of 16 selectable output lines, so long as it is enabled. For the pacemaker application, the timing signal that is being generated may be used for any one of a plurality of purposes, such as generating the output stimulus pulse, generating a blanking signal, etc., and decoder 72 selects the desired output line as a function of the latched 4 bit address. Thus, by programming the starting address of the R(O) pointer, both the duration of the timing signal and the desired control line are selected.

The timing signal from decoder 72 goes high at the time the data word is latched into counter 66, and goes low at a time corresponding to the data content of the word brought from memory. Thus, the length of the timing signal generated from a single data word can be set to within a 25 microsecond interval., i.e. can be varied from 25 microseconds to about 6.1 ms in 25 microsecond intervals. In the top graph of FIG. 4 there is illustrated a single pulse timing signal of 1.6 ms duration, corresponding to a countdown of 64 clocks. In the bottom graph of FIG. 4, there is shown a timing signal composed of 3 "pulses", namely a first pulse of 0.8 ms, a second negative pulse of 0.4 ms, and a third pulse of 0.8 ms. Such a timing signal may be generated by transferring a series of 3 data words during DMA operation, each of which causes a respective pulse to appear on a respective output line from decoder 72. By utilizing gates 73, the timing signal is made to appear on a single control line. The negative pulse portion may be obtained by utilizing an inverter in block 73.

The apparatus and method as have been described thus far are general in scope, as providing for the generation of timing signals to be used in any desired application. While the invention is not so limited, it is illustrated in terms of a pacer application. Still referring to FIG. 2 the upper path shows a timing diagram for controlling the gating of clock signals to the microprocessor. Timer 74 receives clock signals from generator 65. It may be set, under software control as in the programmable pacer application, to time out at a given time T, at which point it provides an enabling input to logic gate 75, the output of which resets flip flop 76. The high inverter output from 76 enables AND gate 77, permitting gating of clock pulses directly from generator 65 through to the microprocessor. Likewise, the microprocessor can turn itself off by causing a high input to be connected to the set terminal of flip flop 76, which disables gate 77. A microprocessor off instruction causes a selected bit of the status word stored at 85 to be changed to a high level ($d_2=1$), from which the set signal for flip flop 76 is obtained. By this means, the microprocessor may be turned off by inhibiting transfer of clock pulses upon a program command from the microprocessor, and may be turned back on upon timing out of a programmed time duration, or any one of a plurality of conditions inputted as at OR gate 75.

In the DMA mode, when a data word is first latched into counter 66 with a TPB pulse, it takes 8 more clocks before the next data word pointed to is transferred onto the data bus and to latch 68. Thus, the clocks must continue to the microprocessor to provide these 8 next clocks, if a next data word is to be delivered. However, if the countdown down of the first data word takes more than 8 clocks, then succeeding clocks must not be passed to the microprocessor or it would fetch the next data pulse. This is handled by the path consisting of switch 64 and flip-flops 78,79. When the first TPB pulse occurs after DMA-Int goes high, switch 64 is switched to connect the output of 79 to the lower input of gate 77. This keeps gate 77 enabled until the next TPB pulse, or 8 cycles later, when 78 is set and 79 is reset, thus turning off the clock to the microprocessor. When counter 66 counts down to zero, 78 is reset and 79 set, permitting another 8 clocks to be gated through to fetch the next data word. Note that when the "stop" address is reached and the corresponding data word is latched into counter 66, the DMA and DMA-Int signals go low, switch 64 goes back to its normal position, and the microprocessor runs continuously until it is stopped by a subsequent instruction. It is to be noted that the logic and timing performed by the path comprising blocks 64, 78, 79 may be performed by different circuitry, the block diagram of FIG. 2 being illustrative only; the specific circuitry is not important to the scope of the invention or to the preferred embodiment.

Referring to FIG. 3, there is shown a single path of a flow diagram of a fixed rate program for use in a pacer application. At the start of the routine, the timer is set to a pacing interval $T_{pi}$ as indicated at block 100. When this is done, the microprocessor is stopped as indicated at block 101, such as by outputting a signal which sets flip flop 76 illustrated FIG. 2. When the timer times out, the microprocessor is started again, and time T is recorded at block 102. At block 103 it is determined whether there has been an accurate time out, and if the answer is yes the timer is reset, as indicated at block 104. Following this, at block 105 the microprocessor causes loading of the pulse width, $T_{pw}$. This step effectively carries out the loading of the stop address as indicated at block 80 in FIG. 2, which limits the series of data words transferred during DMA. Following this, at block 106, the program causes the microprocessor to be set in the DMA mode, by generating a status signal with the $d_4$ bit set equal to one. As this time, the above-described process of generating the timing signal is carried out, utilizing the microprocessor under DMA mode for direct transfer of data words to the controller where the data words are transferred into timing signals. It is to be understood that by this means the full programming capability of the microprocessor and memory can be utilized for generating the timing signals, and yet the apparatus is not limited by the time involved in going through full instruction cycles of the microprocessor. Following generation of the timing signals, certain bookkeeping is done as indicated at block 107, following which there is a determination at block 108 of whether the last signal was a natural beat which reset the timer (not necessary for a fixed rate path), or a delivered pacing stimulus. If it was a delivered pacing stimulus, this fact is remembered at block 109.

As is now evident, there has been illustrated an apparatus and method for generating timing signals under program control of a microprocessor. By use of this invention, a relatively low clock frequency such as 40 KHz may be utilized, permitting low power consumption of the microprocessor, while timing signals can be generated to a resolution of the period of the clock signal, e.g., 25 microseconds for a 40 KHz clock. In applications such as implantable pacers, where programmed time signal resolutions of 0.1 millisecond or less are desirable, the invention permits such signals to be achieved with relatively low power consumption. Further, more complex timing signals for use in blanking circuits and other areas may be generated under software control.

We claim:
1. Pacemaker apparatus utilizing microprocessor DMA for generating timing signals for control of a pacemaker function, comprising a microprocessor having including a DMA controller for carrying out DMA data tranfer operations when microprocessor is in a DMA mode, memory interconnected with said microprocessor and containing a stored program and a plurality of data words stored at predetermined addresses for selection by said microporcessor when in said DMA mode, plurality of circuits including at least one pacing circuit which is controllable by a pacer timing signal, characterized by
a pacemaker controller interconnected with said microprocessor and said memory,
said pacemaker controller having first means for receiving signals from said microprocessor and for setting said mircoprocessor in said DMA mode upon receipt of a predetermined signal generated by said program; second means for receiving transferred data words directly from said memory under control of said microprocessor when said microprocessor is in said DMA mode; third means connected to said second means for generating a two state pacer timing signal corresponding to the data content of one or more such received data; and gate means for connecting said pacer signal to said pacing circuit for control of same.

2. The pacemaker apparatus as described in claim 1, wherein said pacemaker controller comprises sequence means for maintaining said microprocessor in said DMA mode for the transfer of a sequence of said data words, and wherein said timing signal comprises a sequence of timing signals in continuous time series, each of said timing signals corresponding to a respective one of said received data words.

3. The pacemaker apparatus as described in claim 2, wherein said pacing circuit comprises stimulus means for delivering pacing signals to a patient's heart and detecting means for receiving detected signals from said patient.

4. The pacemaker apparatus as described in claim 3, wherein said pacemaker controller comprises timer means for timing out predetermined time intervals, receiving means for receiving interval data from said microprocessor and for setting said timer means to time out an interval corresponding to said data, and gate means connected to said time means for stopping operation of said microprocessor during the timing out of a said interval.

5. The pacemaker apparatus as described in claim 4, wherein said program contains instructions for generating periodic intervals, and said pacemaker controller comprises a clock generator and said gate means normally connects clock signals from said clock generator to said microprocessor.

6. The pacemaker apparatus as described in claim 5, wherein said pacemaker controller comprises DMA signal means for connecting a DMA signal to said gate means for controlling connection of clock pulses to said microprocessor when it is in a DMA mode of operation.

7. The pacemaker apparatus as described in claim 1, wherein said pacemaker controller has stop means for storing a stop address, means for receiving from said microprocessor address data relating to the memory address from which data is being transferred under DMA control, compare means for comparing said stop address with each said transferred address, and control means enabling said transfer to continue until a transferred address compares with said stop address.

8. The pacemaker apparatus as described in claim 1, wherein said third means comprises a counter, means for latching a received data word into said counter, and clock means for clocking said counter to provide an output which varies in time as a function of the latched data word.

9. The pacemaker apparatus as described in claim 8, wherein said gate means comprises a decoder circuit and means for receiving and inputting to said decoder circuit data representative of the address from which said data word was transferred, a plurality of output lines connected from said decoder to respective ones of said circuits, said decoder having logic means for connecting said output to a selected one of said output lines as a function of said address data.

10. The pacemaker apparatus as described in claim 1, comprising means for programming the data content of each of said plurality of data words at said predetermined addresses, and also means for selecting said stop address, thereby programming a series of data words which determine the pulse sequence of said timing signal.

11. The pacemaker apparatus as described in claim 10, wherein said stored data words are arranged in memory so as to provide a time signal with a predetermined sequence of high and low output levels.

12. The pacemaker apparatus as described in claim 8, wherein said data words are n bit words and said counter is an n bit counter, enabling programming of said timing signals to a time resolution equal to the interval of said clock source.

* * * * *

UNITED STATES PATENT AND TRADEMARK OFFICE
CERTIFICATE OF CORRECTION

PATENT NO. : 4,627,022

DATED : December 2, 1986

INVENTOR(S) : Kornelis A. Mensink; Henk L. Brouwer

It is certified that error appears in the above-identified patent and that said Letters Patent is hereby corrected as shown below:

Column 7, line 67, please delete "applicatiohs" and substitute therefor --applications--.

Signed and Sealed this

Tenth Day of March, 1987

Attest:

DONALD J. QUIGG

Attesting Officer

Commissioner of Patents and Trademarks